(12) United States Patent
McLawhorn et al.

(10) Patent No.: US 10,500,029 B2
(45) Date of Patent: Dec. 10, 2019

(54) EXPANDABLE MESH WITH LOCKING FEATURE

(71) Applicant: Cook Medical Technologies LLC, Bloomington, IN (US)

(72) Inventors: Tyler E. McLawhorn, Winston-Salem, NC (US); John C. Sigmon, Jr., Winston-Salem, NC (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 186 days.

(21) Appl. No.: 14/748,992

(22) Filed: Jun. 24, 2015

(65) Prior Publication Data
US 2015/0374475 A1    Dec. 31, 2015

Related U.S. Application Data

(60) Provisional application No. 62/018,986, filed on Jun. 30, 2014.

(51) Int. Cl.
*A61F 2/00* (2006.01)
*B23P 19/00* (2006.01)
*A61B 17/00* (2006.01)

(52) U.S. Cl.
CPC ........ *A61F 2/0063* (2013.01); *A61B 17/0057* (2013.01); *B23P 19/00* (2013.01); *A61B 2017/00407* (2013.01); *A61B 2017/00526* (2013.01); *A61B 2017/00592* (2013.01); *A61B 2017/00619* (2013.01);
(Continued)

(58) Field of Classification Search
CPC ............ A61F 2/0063; A61F 2002/0068; A61F 2220/0033; A61F 2230/0067; A61F 2230/0069; A61F 2220/0075; A61B 17/0057; A61B 2017/00619; A61B 2017/00659; A61B 2017/00592; A61B 2017/00407

See application file for complete search history.

(56) References Cited

U.S. PATENT DOCUMENTS 5,059,193 A * 10/1991 Kuslich ................. F16B 13/061
                                                    606/247
8,257,394 B2 * 9/2012 Saadat ............... A61B 17/0401
                                                    606/232
(Continued)

FOREIGN PATENT DOCUMENTS

EP         1275351         6/2002

OTHER PUBLICATIONS

International Search Report and Written Opinion for PCT/US2015/037378 dated Aug. 7, 2015, 13 pgs.
(Continued)

*Primary Examiner* — Thomas M McEvoy
(74) *Attorney, Agent, or Firm* — Brinks Gilson & Lione

(57) ABSTRACT

The present embodiments provide an expandable mesh comprising a first coupling element, a second coupling element, and an intermediate portion disposed between the first coupling element and the second coupling element. Proximal retraction of the first coupling element relative to the second coupling element causes the intermediate portion to flare out to an enlarged width. In one embodiment, the first coupling element comprises a first tube and the second coupling element comprises a second tube.

12 Claims, 4 Drawing Sheets

(52) U.S. Cl.
CPC ........... *A61B 2017/00659* (2013.01); *A61B 2017/00876* (2013.01); *A61F 2002/0068* (2013.01); *A61F 2220/0033* (2013.01); *A61F 2220/0075* (2013.01); *A61F 2230/0067* (2013.01); *A61F 2230/0069* (2013.01); *A61F 2240/001* (2013.01)

(56) References Cited

U.S. PATENT DOCUMENTS

| | | | |
|---|---|---|---|
| 2002/0169473 A1* | 11/2002 | Sepetka et al. | |
| 2003/0088256 A1* | 5/2003 | Conston | A61B 17/11 606/155 |
| 2003/0167062 A1* | 9/2003 | Gambale | A61B 17/0487 606/138 |
| 2008/0071301 A1 | 3/2008 | Matsuura et al. | |
| 2009/0281557 A1* | 11/2009 | Sander | A61B 17/11 606/151 |
| 2010/0030256 A1 | 2/2010 | Dubrual et al. | |
| 2012/0016409 A1 | 1/2012 | Sherwinter et al. | |
| 2014/0257374 A1* | 9/2014 | Heisel et al. | |
| 2015/0032153 A1* | 1/2015 | Quadri | A61B 17/0057 606/215 |

OTHER PUBLICATIONS

Communication pursuant to Rules 161(1) and 162 EPC for European Patent Application No. 15734001.9 dated Feb. 15, 2017, 2 pgs.
Response to Communication pursuant to Rules 161(1) and 162 EPC for European Patent Application No. 15734001.9 filed Aug. 23, 2017, 9 pgs.
Examination Report for EP15734001.9 dated Sep. 25, 2018, 5 pgs.

\* cited by examiner

EXPANDABLE MESH WITH LOCKING FEATURE

PRIORITY CLAIM

This invention claims the benefit of priority of U.S. Provisional Application Ser. No. 62/018,986, entitled "Expandable Mesh with Locking Feature," filed Jun. 30, 2014, which is hereby incorporated by reference in its entirety.

BACKGROUND

The present embodiments relate generally to medical devices, and more particularly, to an expandable mesh that may be used in a variety of procedures.

There are many instances in which it may be desirable to deliver an expandable mesh into a human or animal body. By way of example, and without limitation, such expandable meshes may be used to treat perforations in tissue or bodily walls that are formed intentionally or unintentionally.

For example, an unintentional abdominal hernia may be formed in the abdominal wall due to heavy lifting, coughing, strain imposed during a bowel movement or urination, fluid in the abdominal cavity, or other reasons. Intentional perforations may be formed, for example, during surgical procedures such as translumenal procedures. In a translumenal procedure, one or more instruments, such as an endoscope, may be inserted through a visceral wall, such as the stomach wall. During a translumenal procedure, a closure instrument may be used to close the perforation in the visceral wall. Depending on the structure comprising the perforation, it may be difficult to adequately close the perforation and prevent leakage of bodily fluids.

Attempts to seal perforations have been made by coupling a graft member to tissue. For example, during hernia repair, a graft material such as a mesh or patch may be disposed to cover the perforation. The graft material may completely overlap with the perforation, and the edges of the graft material may at least partially overlap with tissue surrounding the perforation. The graft material then may be secured to the surrounding tissue in an attempt to effectively cover and seal the perforation.

In order to secure the graft material to the surrounding tissue, sutures commonly are manually threaded through the full thickness of the surrounding tissue. In the case of an abdominal hernia, the sutures may be threaded through the thickness of the abdominal wall, then tied down and knotted. However, such manual suturing techniques may be time consuming and/or difficult to perform.

There is also a hernia repair method commonly referred to as a "mesh plug" or "plug and patch" repair technique, in which a surgeon uses a mesh plug to fill the perforation. Potential advantages include fewer sutures and less tissue dissection. However, a mesh plug alone may not effectively cover the entire area of the perforation, or alternatively, the mesh plug may shrink, become loose, or poke into the bladder or intestines.

SUMMARY

The present embodiments provide an expandable mesh comprising a first coupling element, a second coupling element, and an intermediate portion disposed between the first coupling element and the second coupling element. Proximal retraction of the first coupling element relative to the second coupling element causes the intermediate portion to flare out to an enlarged width.

In one embodiment, the first coupling element comprises a first tube and the second coupling element comprises a second tube. In one example, the first tube, the second tube, and the intermediate portion each originate from the same mesh material. In one example, the intermediate portion comprises untreated mesh material, and the first and second tubes are formed from treating the mesh material in a manner that maintains a tubular shape of the first and second tubes. At least one of the first tube or the second tube may be formed by melting or heat-shrinking the mesh material.

The expandable mesh may comprise a delivery state in which the first and second tubes lack an axial overlap, and further may comprise an expanded state in which the first and second tubes at least partially axially overlap. In one embodiment, a distal end of the first tube transitions into a first end of the intermediate portion, and a second end of the intermediate portion transitions into a distal end of the second tube.

The expandable mesh may comprise first and second ends. In one example, the expandable mesh may have a first state in which the first end is positioned proximal to the second end, and an everted second state in which the second end is positioned proximal to the first end.

The first and second tubes may be dimensioned to be secured together using a friction fit when the first tube is proximally retracted relative to the second tube. In one embodiment, one of the first and second tubes comprises a constant diameter along its length, while the other of the first and second tubes comprises a tapered shape. In an alternative embodiment, both the first and second tubes comprise tapered shapes, wherein the first tube is dimensioned to be disposed at least partially within the second tube when the first tube is proximally retracted relative to the second tube.

A system may be used with the expandable mesh. The system may comprise a first tether secured to the first coupling element, wherein proximal retraction of the first tether causes proximal retraction of the first coupling element relative to the second coupling element. Further, the system may comprise a graft material having a first bore formed therein, wherein the first bore is dimensioned for advancement over the first tether to permit the graft material to be advanced relative to the first coupling element.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

In the present application, the term "proximal" refers to a direction that is generally towards a physician during a medical procedure, while the term "distal" refers to a direction that is generally towards a target site within a patent's anatomy during a medical procedure. Thus, "proximal" and "distal" portions of a device or bodily region may depend on the point of entry for the procedure (e.g., percutaneously versus laparoscopically or endoscopically).

Additionally, it is noted that when manufacturing a device according to one embodiment, an eversion step is performed whereby a portion that was originally a distal region of the device becomes a proximal region. For clarity, the region that is originally near a proximal end will be referred to as the first end, while the region that is originally near a distal end will be referred to as the second end.

Figure 1:
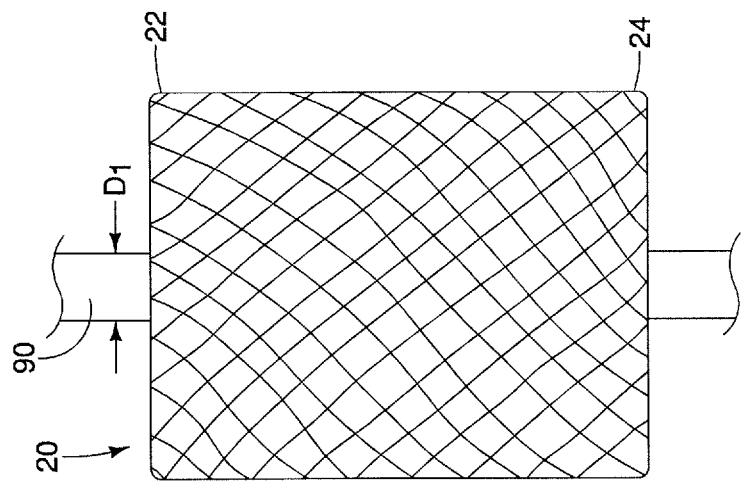
FIG. 1 is a side view of a mesh disposed over a first mandrel.

Referring to FIG. 1, a mesh 20 having a first end 22 and a second end 24 is provided. The mesh 20 may be disposed over a first mandrel 90 having an outer diameter $D_1$, such that the first end 22 is initially disposed proximal to the second end 24, as shown in FIG. 1.

The mesh 20 can be fashioned from absorbable or non-absorbable mesh or biologic implant. By way of example, and without limitation, the mesh material may comprise polypropylene, polyethylene, glycolide/L-lactide copolymer, PTFE, nylon, polyurethane, PEEK, PLGA, PGA, polycaprolactone, carbothane, polydioxanone, or any copolymer of the aforementioned list.

Figure 2:
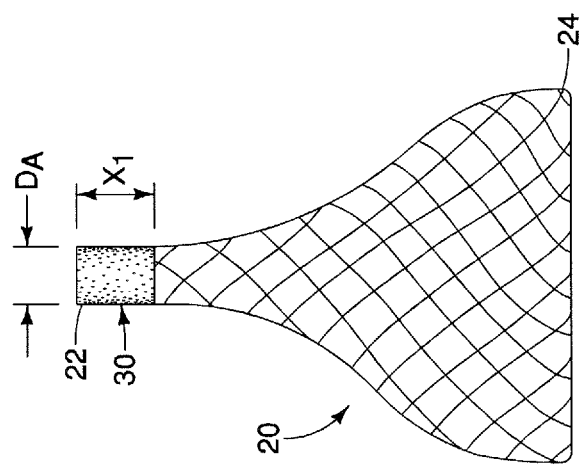
FIG. 2 is a side view of the mesh after formation of a first tube.

Referring to FIG. 2, in a next step, the first end 22 of the mesh 20 is made to form a first coupling element 30. In this example, the first coupling element 30 is in the form of a first tube 30. However, it will be appreciated that the first coupling element 30 may take a form different than a tubular shape. For reference purposes below, the first coupling element 30 will be referenced as a first tube 30, although it is not intended to limit the shape of the first coupling element 30 to tubular form.

Since the first tube 30 is formed around the first mandrel 90, the first tube 30 comprises an inner diameter that is only slightly larger than the outer diameter $D_1$ of the first mandrel 90. Further, the first tube 30 comprises an outer diameter $D_A$, as shown in FIG. 2.

The first tube 30 is formed such that it comprises a length $X_1$, as shown in FIG. 2. In a presently preferred embodiment, the length $X_1$ is less than half of the overall length of the mesh 20, where the overall length is measured between the most proximal and distal endpoints of the mesh 20 in a flattened state of FIG. 1. Preferably, the length $X_1$ of the first tube 30 is between about 5.0 percent and about 33.0 percent of the overall length of the mesh 20 in the flattened state. In this manner, the length $X_1$ of the first tube 30 can most effectively cooperative with a subsequently formed second tube 40 and an intermediate portion 50, as will be explained further below.

In one exemplary technique, the first end 22 of the mesh 20 may be secured as the first tube 30 by melting or heat-shrinking the mesh material upon itself along the first end 22. In alternative embodiments, the first end 22 of the mesh 20 may be secured as the first tube 30 using a separate biocompatible adhesive, one or more biocompatible sutures, or other mechanisms that can maintain the structural integrity of the tubular shape for the purposes explained below.

Figure 3:
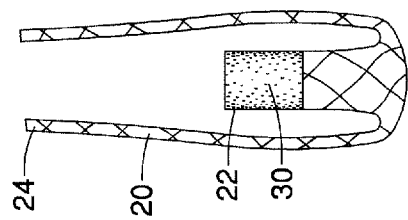
FIG. 3 illustrates eversion of a portion of the mesh, with the first tube depicted in a side view and other mesh material shown in a side-sectional view.

Referring now to FIG. 3, in a next step, the mesh 20 may be at least partially everted by moving the second end 24 proximally beyond the first end 22. In this manner, the second end 24 is brought radially over and around the first tube 30, as shown in FIG. 3. Therefore, in this eversion step, the second end 24 of the mesh 20 that was originally a distal region of the device has become a proximal region.

Figure 5:
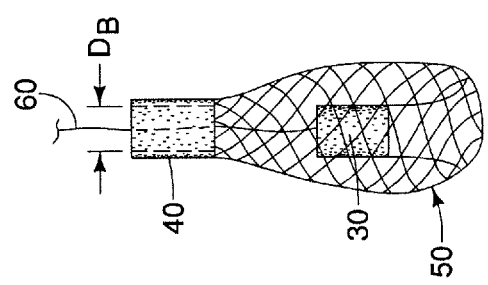
FIGS. 4-5 illustrate exemplary method steps, with first and second tubes depicted in a side view and other mesh material also shown in a side view.
Figure 4:
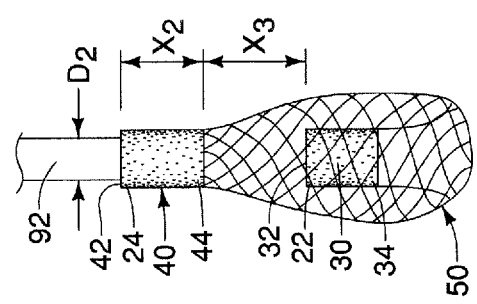

Referring to FIGS. 4-5, the second end 24 then is made into a second coupling element 40, for example, in a manner similar to which the first end 22 was made into the first coupling element 30. In this example, the second coupling element 40 is in the form of a second tube 40. However, it will be appreciated that the second coupling element 40 may take a form different than a tubular shape. For example, the second coupling element 40 may comprise a solid inner diameter, and still may engage an inner surface of the first coupling element 30 using a friction fit, as explained below. For reference purposes below, the second coupling element 40 will be referenced as a second tube 40, although it is not intended to limit the shape of the second coupling element 40 to tubular form.

In one embodiment, the mesh 20 is disposed over a second mandrel 92 having an outer diameter $D_2$, as shown in FIG. 4. Upon manufacture, the second tube 40 comprises an inner diameter $D_B$, as shown in FIG. 5, which is only slightly larger than the outer diameter $D_2$ of the second mandrel 92. Like the first tube 30, the second tube 40 may be secured in the tubular manner by melting or heat-shrinking the mesh material upon itself along the second end 24, or alternatively, by using a separate biocompatible adhesive, one or more biocompatible sutures, or other mechanisms that can maintain the structural integrity of the tubular shape for the purposes explained below.

The outer diameter $D_A$ of the first tube 30 is dimensioned to engage the inner diameter $D_B$ of the second tube 40 using a friction fit, as explained further in FIG. 7 below. To accomplish the friction fit, the outer diameter $D_A$ of the first tube 30 may be approximately equal to the inner diameter $D_B$ of the second tube 40, thereby allowing the outer diameter $D_A$ of the first tube 30 to snugly engage the inner diameter $D_B$ of the second tube 40. In the embodiment of FIGS. 1-9, the first and second tubes 30 and 40 are depicted as being generally cylindrical with constant diameters along their lengths. In the alternative embodiments of FIGS. 10A-10C below, various alternative configurations of the first and second tubes 30 and 40 are described.

Referring still to FIGS. 4-5, the second end 24 of the mesh 20 is secured in the tubular manner such that the second tube 40 comprises a length $X_2$. In one embodiment, the length $X_2$ is less than half of the overall length of the mesh 20, where (as noted above) the overall length is measured between the most proximal and distal endpoints of the mesh 20 in a flattened state of FIGS. 1-2. Preferably, the length $X_2$ of the second tube 40 is between about 10.0 percent and about 38.0 percent of the overall length of the mesh 20 in the flattened state.

An intermediate portion 50 of the mesh 20, which is neither part of the first tube 30 nor the second tube 40, remains after formation of the first and second tubes 30 and 40. The intermediate portion 50 of the mesh 20 may comprise the original mesh material, e.g., untreated by heat or other techniques used to form the tubes 30 and 40, and spans from the distal end 34 of the first tube 30 to the distal end 44 of the second tube 40, as shown in FIG. 4.

The intermediate portion 50 of the mesh 20 includes the everted portion of the mesh, as shown in FIGS. 4-5, and may comprise between about 29.0 percent to about 85.0 percent of the overall length of the mesh 20, i.e., the total length of the mesh 20 minus the lengths of the first and second tubes 30 and 40. The desired length of the intermediate portion 50 of the mesh 20 may be selected based on a particular application, for example, closure of a bodily opening of a certain diameter. As will be explained further with respect to FIGS. 7-9, the intermediate portion 50 of the mesh 20 will flare radially outward to a width w to perform its intended purpose. As will be understood, the final deployed width w of the device is related to the overall length of the intermediate portion 50, i.e., if the length of the intermediate portion 50 is relatively large then the device can flare to a relatively large width w, whereas if the length of the intermediate portion 50 is relatively small then the device can flare to a relatively small width w.

Further, it is noted that an axial spacing $X_3$ is provided between the first and second tubes 30 and 40, as shown in FIGS. 4-5. The spacing $X_3$ provides a distance for retraction of the first tube 30 relative to the second tube 40, as explained further in FIG. 7 below. By varying the spacing $X_3$, the deployed width w of the intermediate portion 50 may be varied accordingly. For example, if a relatively large axial spacing $X_3$ is provided, then the first tube 30 must be retracted a relatively long distance before securely engaging the second tube 40, and during this relatively long distance the intermediate portion 50 has additional time and length to flare out to a greater width w.

Figure 6:
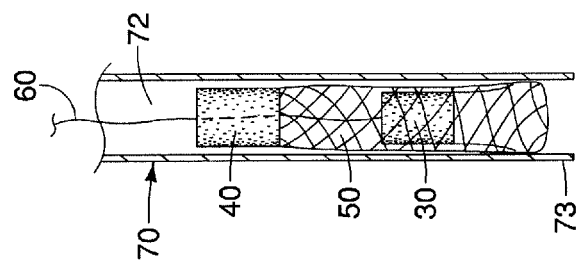
FIG. 6 illustrates the mesh in a delivery state, with the mesh shown in a side view and an insertion tool shown in a side-sectional view.
Figure 7:
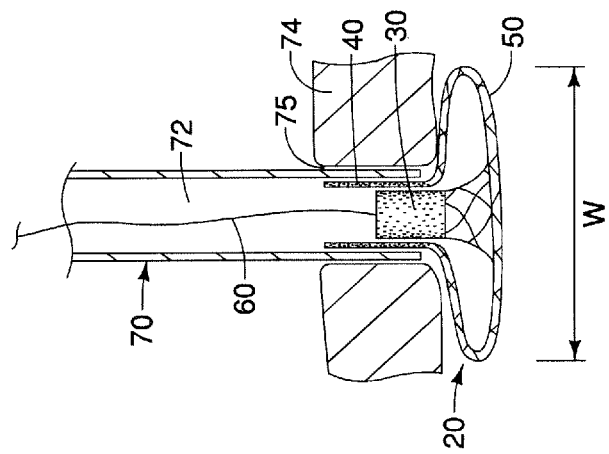
FIG. 7 illustrates deployment of the mesh, with the first tube depicted in a side view, and the second tube, other mesh material and the insertion tool shown in side-sectional views.

Referring to FIGS. 5-6, a first tether 60 is coupled to the first tube 30, either on an inner or outer surface of the first tube 30. The first tether 60 extends proximally from the first tube 30, is disposed through the second tube 40, and extends further proximally along a length of an insertion tool 70 for actuation by a physician. A distal region of the first tether 60 may be coupled to the first tube 30 using an adhesive, mechanical member or other suitable techniques.

In a delivery state, the mesh 20 is housed within a lumen 72 of the insertion tool 70, as shown in FIG. 6. The insertion tool 70 may comprise a catheter, needle or other suitable insertion member. If a needle is used, it may be an endoscopic ultrasound (EUS) or echogenic needle, such as the EchoTip® Ultrasound Needle, or the EchoTip® Ultra Endoscopic Ultrasound Needle, both manufactured by Cook Endoscopy of Winston-Salem, N.C.

The insertion tool 70 may be advanced to a target site using various known techniques, depending on the desired treatment modality. For example, and without limitation, in one embodiment the mesh 20 may be used to treat an opening 75 of a hernia within tissue 74 of the abdominal wall, as depicted in FIG. 7. While treatment of a hernia is explained for illustrative purposes, it will be apparent that the systems described herein may be used in a wide range of medical procedures, including but not limited to any exemplary procedures described herein.

The initial stages of the hernia repair may be performed using various techniques, for example, an open technique, a laraposcopic technique, an endoscopic technique, or a percutaneous technique. In an open technique, an incision may be made in the abdominal wall and the hernia may be repaired using generally known principles.

In a laparoscopic technique, two or three smaller incisions may be made to access the hernia site. A laparoscope may be inserted into one incision, and surgical instruments may be inserted into the other incision(s) and the hernia may be repaired in a similar fashion as the open procedure.

In an endoscopic technique, an endoscope is used instead of the laparoscopic devices, and no visible incisions may be made on the skin of the patient. In particular, the endoscope may be advanced through a bodily lumen such as the alimentary canal, with an access hole being created through the alimentary canal, to obtain peritoneal access to the hernia. One or more components, such as the insertion tool 70, may be advanced through a working lumen of the endoscope. The distal end of the insertion tool 70 may be viewed via optical elements of the endoscope, which may comprise fiber optic components for illuminating and capturing an image distal to the endoscope.

The percutaneous approach is similar to the laparoscopic approach, however, in the percutaneous approach the insertion tool 70 may be advanced directly through a patient's abdominal skin. In particular, with the components loaded, the insertion tool 70 is advanced directly through the abdominal skin, through the tissue 74, and may be advanced just distal to the opening 75 and into the peritoneum. In order to optimally visualize the insertion tool 70, a laparoscopic viewing device may be positioned in the peritoneum, or an endoscope may be translumenally advanced in proximity to the target site, as noted above. Alternatively, the insertion tool 70 and markers disposed thereon may be viewed using fluoroscopy of other suitable techniques.

After gaining access to the opening 75 or target site using any of the above-referenced techniques, the insertion tool 70 may be used to deliver the mesh 20. The mesh 20 may be advanced within the lumen 72 of the insertion tool 70, e.g., using a stylet, and then may be positioned such that the second tube 40 is aligned near the distal end 73 of the insertion tool 70. At this time, a majority of the intermediate portion 50 of the mesh 20 may be disposed distally beyond the distal end 73 of the insertion tool 70. As will be appreciated, the distal end 73 of the insertion tool 70, and any of the first and second tubes 30 and 40, may comprise radiopaque markers or features that facilitate visualization of relative components positions by a physician during such delivery.

Referring to FIG. 7, in a next step, the first tether 60 is retracted proximally to cause the first tube 30 to be retracted proximally relative to the second tube 40. Optionally, a stylet may be provided within the lumen 72 of the insertion tool 70 to abut the proximal end 42 of the second tube 40 to hold it steady during retraction of the first tether 60 and coupled first tube 30. This causes the first tube 30 to engage the second tube 40, as depicted in FIG. 7.

As the first tether 60 is proximally retracted and the first tube 30 is retracted proximally relative to the second tube 40, the intermediate portion 50 of the mesh 20 expands radially outward to the width w, as depicted in FIG. 7. Locking of the first and second tubes 30 and 40 relative to one another consequently fixes the width w of the intermediate portion 50, and therefore the intermediate portion 50 is retained in its deployed state.

As explained in detail above, the first and second tubes 30 and 40 may comprise diameters that are dimensioned to securely engage each other with a friction fit, and may comprise constant diameters or tapered shapes to facilitate a secure engagement upon retraction of the first tube 30 relative to the second tube 40. A secure engagement between the first and second tubes 30 and 40 therefore may be provided.

Figure 10C:
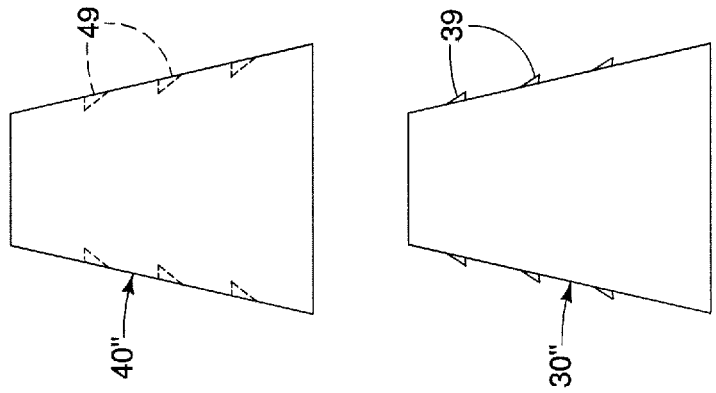
FIGS. 10A-10C are side views of alternative first and second tube configurations.

In addition to, or in lieu of, the friction fit noted above, another locking mechanism may be used to securely hold the first and second tubes 30 and 40 relative to each other. For example, and without limitation, an exterior surface of the first tube 30 may engage an interior surface of the second tube 40 using a one-way ratcheting mechanism, which can permit incremental securement to incrementally adjust the width w of the intermediate portion 50 of the mesh 20. An example of interlocking components 39 and 49 of a ratchet arrangement is shown in the embodiment of FIG. 10C below.

If the mesh 20 is used to treat the opening 75 of a hernia within tissue 74 of the abdominal wall, the intermediate portion 50 of the mesh 20 may be anchored within the opening 75 of the hernia and/or distal to the opening 75. If deployed within the opening 75, the width w of the mesh 20 may be larger than an inner diameter of the opening 75 to secure the mesh 20 within the opening 75 using a friction fit. Alternatively, the mesh 20 may be deployed distal to the opening 75, as depicted in FIGS. 7-8, in which case the mesh 20 can assume a diameter larger than the opening 75 and provide anchoring functionality just distal to the tissue 74.

Figure 9:
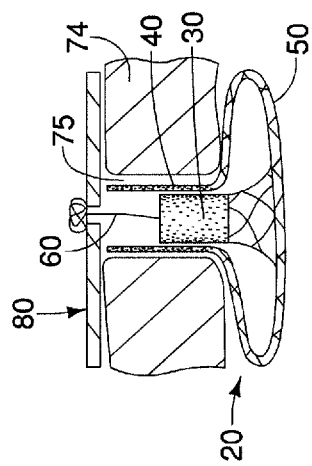
FIGS. 8-9 illustrate advancement of a graft member over a first tether coupled to the mesh, with the first tube depicted in a side view, and the second tube, other mesh material and the insertion tool shown in side-sectional views.
Figure 8:
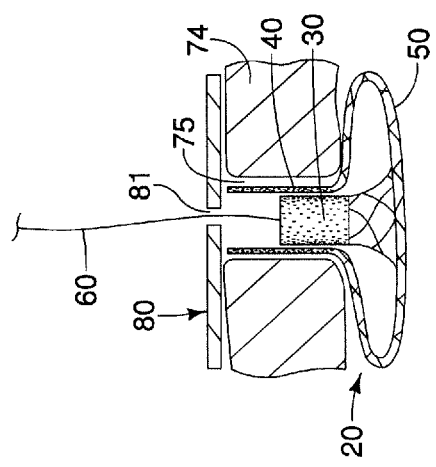

Referring to FIGS. 8-9, in a next step, a graft member 80 may be advanced distally over the first tether 60 towards the mesh 20. Properties of suitable graft members 80 are described in detail below. The graft member 80 comprises a first bore 81, which is sized to permit advancement of the graft member 80 over the first tether 60.

In use, the proximal end of the first tether 60 is disposed through the first bore 81 of the graft member 80 outside of the patient, and the graft member 80 is advanced distally relative to the first tether 60. The graft member 80 may be delivered through the insertion tool 70. Alternatively, the graft member 80 may be delivered directly through a trocar, e.g., a 5 mm trocar. When ejected from the insertion tool 70 or the trocar, the graft member 80 then is positioned in place relative to the tissue 74 using a suitable grasping device, or a pusher tube or the insertion tool 70 itself, such that the graft member 80 is adjacent to the tissue 74 and covering the opening 75, as shown in FIG. 8. In a next step, a suture tying device may be used to tie a knot for the first tether 60 to hold the graft member 80 in place.

Optionally, a second tether (not shown) may be provided in a similar manner to the first tether 60. In this embodiment, the graft member 80 may comprise a second bore, whereby the first bore 81 of the graft member 80 is advanced over the first tether 60 and the second bore of the graft member 80 is simultaneously advanced over the second tether. In this example, a suture tying device may be used to tie the first and second tethers together in a manner that secures the graft member 80 adjacent to the tissue 74 and the mesh 20. By way of example, and without limitation, one suitable suture tying device is disclosed in U.S. Pat. No. 8,740,937, the disclosure of which is hereby incorporated by reference in its entirety. Upon completion of the tying procedure, the one or more tethers may be cut by a suitable device, such as laparoscopic scissors, leaving the mesh 20 and the graft member 80 in place as shown in FIG. 9.

Advantageously, using the mesh 20, the first tether 60 (and optionally a second tether), and the graft member 80 in combination, along with the techniques described, an enhanced mesh anchoring and graft member attachment may be achieved to comprehensively treat the opening 75. Further, the coupling of the mesh 20 to the graft member 80 provides an enhanced seal relative to a plug alone, and the secure attachment of the mesh 20 to the graft member 80 may further reduce the rate of migration of the mesh 20.

The graft member 80 may comprise any suitable material for covering the opening 75 and substantially or entirely inhibiting the protrusion of abdominal matter. In one embodiment, the graft member 80 may comprise small intestinal submucosa (SIS), such as BIODESIGN® SURGISIS® Tissue Graft, available from Cook Biotech, Inc., West Lafayette, Ind., which provides smart tissue remodeling through its three-dimensional extracellular matrix (ECM) that is colonized by host tissue cells and blood vessels, and provides a scaffold for connective and epithelial tissue growth and differentiation along with the ECM components. The graft member 80 may be lyophilized, or may comprise a vacuum pressed graft that is not lyophilized. In one example, the graft member 80 would be a one to four layer lyophilized soft tissue graft made from any number of tissue engineered products. Reconstituted or naturally-derived collagenous materials can be used, and such materials that are at least bioresorbable will provide an advantage, with materials that are bioremodelable and promote cellular invasion and ingrowth providing particular advantage. Suitable bioremodelable materials can be provided by collagenous ECMs possessing biotropic properties, including in certain forms angiogenic collagenous extracellular matrix materials. For example, suitable collagenous materials include ECMs such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa, including small intestinal submucosa, stomach submucosa, urinary bladder submucosa, and uterine submucosa. The graft member 80 may also comprise a composite of a biomaterial and a biodegradeable polymer. Additional details may be found in U.S. Pat. No. 6,206,931 to Cook et al., the disclosure of which is incorporated herein by reference in its entirety.

While the exemplary embodiments herein have illustrated the use of an expandable mesh 20 for covering an opening 75 formed in the abdominal wall, the expandable mesh 20 disclosed herein may be useful in many other procedures. Solely by way of example, the expandable mesh 20 may be used to treat perforations in a visceral wall, such as the stomach wall, or could be used to treat heart defects, to prevent a duodenal sleeve from migrating, for securing a graft member to tissue for reconstructing local tissue, or various other procedures that can benefit from such an expandable mesh.

Figure 10B:
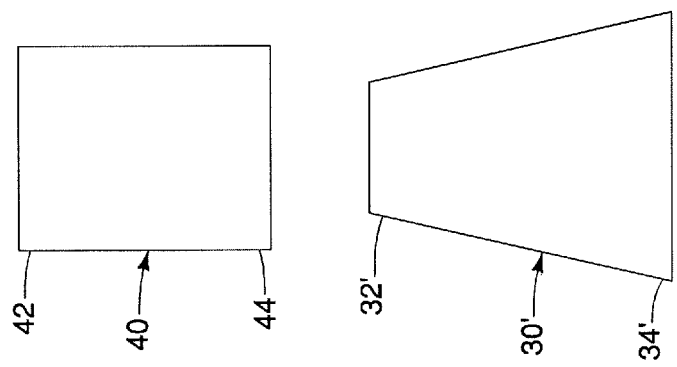
Figure 10A:
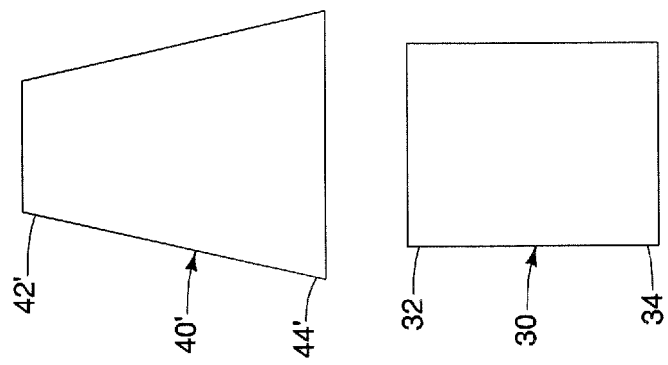

Referring to FIGS. 10A-10C, alternative embodiments are shown in which the first tube 30 and/or the second tube 40 lack constant diameters. In the embodiment of FIG. 10A, an alternative second tube 40' comprises a tapered shape between proximal and distal ends 42' and 44', wherein the distal end 44' has an inner diameter than is larger than an inner diameter of the proximal end 42'. In this embodiment of FIG. 10A, the inner diameter of the distal end 44' of the second tube 40' may be larger than the outer diameter $D_A$ of the first tube 30 to allow the first tube 30 to be proximally retracted within the distal portion of the second tube 40, however, the inner diameter of the proximal end 42' of the second tube 40' may be smaller than the outer diameter $D_A$ of the first tube 30 so that the first tube 30 could not be proximally retracted beyond the proximal end 42' of the second tube 40'. In this manner, the first tube 30 may frictionally engage a region of the second tube 40' between the proximal and distal ends 42' and 44'.

In a further alternative embodiment of FIG. 10B, an alternative first tube 30' may comprise a tapered shape between its proximal and distal ends 32' and 34'. A diameter at the proximal end 32' is smaller than a diameter at the distal end 34' to permit retraction into the second tube 40.

In the embodiment of FIG. 10C, both first and second tubes 30" and 40" are tapered with proximal diameters being smaller than distal diameters. Further, in the embodiment of FIG. 10C, an exterior surface of the first tube 30" may engage an interior surface of the second tube 40" using a one-way ratcheting mechanism using interlocking components 39 and 49. Such a one-way ratcheting mechanism can permit incremental securement to incrementally adjust the width w of the intermediate portion 50 of the mesh 20. In addition to the friction fit and one-way ratcheting mechanism options, it is contemplated that other coupling methods may be used to secure the first and second tubes together, including but not limited to magnetic couplings, knobs or beads that interlock in notches, or other mechanical arrangements.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A system for deploying an expandable mesh, comprising:
   an insertion tool;
   an expandable mesh comprising a first coupling element, a second coupling element, and an intermediate portion disposed between the first coupling element and the second coupling element, wherein the expandable mesh comprises first and second ends, and further has a first state in which the first end is positioned proximal to the second end, and an everted second state during delivery within the insertion tool in which the second end is positioned proximal to the first end,
   wherein proximal retraction of the first coupling element relative to the second coupling element causes the intermediate portion to flare out to an enlarged width, wherein there is an interference fit between the first and second coupling elements upon the proximal retraction of the first coupling element relative to the second coupling element, wherein, during the interference fit, a proximal end of the first coupling element is distal to a proximal end of the second coupling element, and
   wherein the first state occurs before the second state.

2. The system of claim 1, wherein the first coupling element comprises a first tube, and wherein the second coupling element comprises a second tube.

3. The system of claim 2, wherein the first tube, the second tube, and the intermediate portion each originate from the same mesh material.

4. The system of claim 3, wherein the intermediate portion comprises untreated mesh material, and wherein the first and second tubes are formed from treating the mesh material in a manner that maintains a tubular shape of the first and second tubes.

5. The system of claim 3, wherein at least one of the first tube or the second tube is formed by melting or heat-shrinking the mesh material.

6. The system of claim 2, wherein the expandable mesh comprises a delivery state in which the first and second tubes lack an axial overlap, and further comprises an expanded state in which the first and second tubes at least partially axially overlap.

7. The system of claim 2, wherein a distal end of the first tube transitions into a first end of the intermediate portion, and a second end of the intermediate portion transitions into a distal end of second tube.

8. The system of claim 2, wherein one of first and second tubes comprises a constant diameter along its length, while the other of the first and second tubes comprises a tapered shape.

9. The system of claim 2, wherein both the first and second tubes comprise tapered shapes, wherein the first tube is dimensioned to be disposed at least partially within the second tube when the first tube is proximally retracted relative to the second tube.

10. The system of claim 1, further comprising a first tether secured to the first coupling element, wherein proximal retraction of the first tether causes proximal retraction of the first coupling element relative to the second coupling element.

11. The system of claim 1, wherein the first end is disposed within the intermediate portion in the everted second state during delivery within the insertion tool.

12. The system of claim 1, wherein eversion occurs before formation of the second coupling element.

* * * * *